(12) United States Patent
Mishra et al.

(10) Patent No.: US 11,766,561 B2
(45) Date of Patent: Sep. 26, 2023

(54) METHODS AND SYSTEMS FOR TREATING PELVIC DISORDERS AND PAIN CONDITIONS

(71) Applicant: Nalu Medical, Inc., Carlsbad, CA (US)

(72) Inventors: Lakshmi Narayan Mishra, Carlsbad, CA (US); Lee Fason Hartley, Carlsbad, CA (US); James C. Makous, Carlsbad, CA (US); Andre Castillo, Encinitas, CA (US); Christopher Linden, Vista, CA (US)

(73) Assignee: Nalu Medical, Inc., Carlsbad, CA (US)

( * ) Notice: Subject to any disclaimer, the term of this patent is extended or adjusted under 35 U.S.C. 154(b) by 0 days.

(21) Appl. No.: 16/222,959

(22) Filed: Dec. 17, 2018

(65) Prior Publication Data

US 2019/0151659 A1 May 23, 2019

Related U.S. Application Data

(63) Continuation of application No. PCT/US2017/042351, filed on Jul. 17, 2017.

(60) Provisional application No. 62/363,742, filed on Jul. 18, 2016.

(51) Int. Cl.
*A61N 1/36* (2006.01)
*A61N 1/372* (2006.01)
*A61N 1/05* (2006.01)

(52) U.S. Cl.
CPC ....... *A61N 1/36007* (2013.01); *A61N 1/0551* (2013.01); *A61N 1/36021* (2013.01); *A61N 1/36071* (2013.01); *A61N 1/37247* (2013.01); *A61N 1/0553* (2013.01); *A61N 1/36017* (2013.01); *A61N 1/37229* (2013.01)

(58) Field of Classification Search
None
See application file for complete search history.

(56) References Cited

U.S. PATENT DOCUMENTS

| | | |
|---|---|---|
| 3,902,501 A | 9/1975 | Citron et al. |
| 3,939,843 A | 2/1976 | Smyth |
| 4,033,357 A | 7/1977 | Helland et al. |
| 4,236,529 A | 12/1980 | Little |
| 4,262,678 A | 4/1981 | Stokes |
| 4,269,198 A | 5/1981 | Stokes |

(Continued)

FOREIGN PATENT DOCUMENTS

| | | |
|---|---|---|
| EP | 2155330 B1 | 10/2014 |
| WO | WO-2005105201 A2 | 11/2005 |

(Continued)

OTHER PUBLICATIONS

PCT/US17/42351 International Search Report dated Sep. 26, 2017.

(Continued)

*Primary Examiner* — Ankit D Tejani
(74) *Attorney, Agent, or Firm* — Cooley LLP

(57) ABSTRACT

A stimulation system comprising: an implantable lead having a proximal end and a distal end, and at least one electrode along its distal end; an implantable neuromodulation stimulator disposed along the proximal end of the implantable lead; and an external device comprising a battery, a transmitter, and an antenna. The implantable lead is integral to the implantable neuromodulation stimulator. Methods of providing stimulation are also described.

30 Claims, 7 Drawing Sheets

(56) References Cited

U.S. PATENT DOCUMENTS

| | | |
|---|---|---|
| 4,301,815 A | 11/1981 | Doring |
| 4,407,303 A | 10/1983 | Akerstroem |
| 4,409,994 A | 10/1983 | Doring |
| 4,469,104 A | 9/1984 | Peers-Trevarton |
| 4,506,679 A | 3/1985 | Mann |
| 4,582,069 A | 4/1986 | McArthur |
| 4,592,356 A | 6/1986 | Gutierrez |
| 4,658,835 A | 4/1987 | Pohndorf |
| 4,716,888 A | 1/1988 | Wesner |
| 4,721,118 A | 1/1988 | Harris |
| 4,796,643 A | 1/1989 | Nakazawa et al. |
| 4,841,971 A | 6/1989 | Hess |
| 4,883,070 A | 11/1989 | Hanson |
| 4,898,173 A | 2/1990 | Daglow et al. |
| 4,945,922 A | 8/1990 | Van Krieken |
| 4,957,118 A | 9/1990 | Erlebacher |
| 5,031,618 A | 7/1991 | Mullett |
| 5,143,067 A | 9/1992 | Rise et al. |
| 5,193,539 A | 3/1993 | Schulman et al. |
| 5,257,634 A | 11/1993 | Kroll |
| 5,282,845 A | 2/1994 | Bush et al. |
| 5,300,107 A | 4/1994 | Stokes et al. |
| 5,545,206 A | 8/1996 | Carson |
| 5,662,697 A | 9/1997 | Li et al. |
| 5,735,887 A | 4/1998 | Barreras, Sr. et al. |
| 5,807,397 A | 9/1998 | Barreras |
| 5,814,089 A | 9/1998 | Stokes |
| 5,833,603 A | 11/1998 | Kovacs |
| 5,868,741 A | 2/1999 | Chia et al. |
| 5,908,433 A | 6/1999 | Eager et al. |
| 5,957,965 A | 9/1999 | Moumane et al. |
| 6,021,354 A | 2/2000 | Warman et al. |
| 6,141,591 A | 10/2000 | Lenarz et al. |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,275,737 B1 | 8/2001 | Mann |
| 6,304,786 B1 | 10/2001 | Heil, Jr. et al. |
| 6,324,434 B2 | 11/2001 | Coe et al. |
| 6,405,091 B1 | 6/2002 | Vachon et al. |
| 6,482,152 B2 | 11/2002 | Kim et al. |
| 6,510,347 B2 | 1/2003 | Borkan |
| 6,516,227 B1 | 2/2003 | Meadows |
| 6,522,926 B1 | 2/2003 | Kieval et al. |
| 6,561,975 B1 | 5/2003 | Pool et al. |
| 6,884,122 B2 | 4/2005 | Robinson et al. |
| 6,895,280 B2 | 5/2005 | Meadows et al. |
| 6,909,917 B2 | 6/2005 | Woods et al. |
| 6,950,706 B2 | 9/2005 | Rodriguez et al. |
| 6,999,819 B2 | 2/2006 | Swoyer et al. |
| 7,092,763 B1 | 8/2006 | Griffith et al. |
| 7,096,070 B1 | 8/2006 | Jenkins et al. |
| 7,239,921 B2 | 7/2007 | Canfield et al. |
| 7,711,419 B2 | 5/2010 | Armstrong et al. |
| 7,717,848 B2 | 5/2010 | Heruth et al. |
| 7,734,340 B2 | 6/2010 | De Ridder |
| 7,734,354 B1 | 6/2010 | Cox |
| 7,742,818 B2 | 6/2010 | Dinsmoor et al. |
| 7,801,615 B2 | 9/2010 | Meadows et al. |
| 7,899,550 B1 | 3/2011 | Doan et al. |
| 7,912,555 B2 | 3/2011 | Swoyer et al. |
| 7,925,357 B2 | 4/2011 | Phillips et al. |
| 7,991,479 B2 | 8/2011 | Phillips et al. |
| 8,000,805 B2 | 8/2011 | Swoyer et al. |
| 8,036,756 B2 | 10/2011 | Swoyer et al. |
| 8,224,453 B2 | 7/2012 | De Ridder |
| 8,364,273 B2 | 1/2013 | De Ridder |
| 8,369,959 B2 | 2/2013 | Meskens |
| 8,401,655 B2 | 3/2013 | De |
| 8,423,147 B2 | 4/2013 | Alataris et al. |
| 8,437,853 B2 | 5/2013 | Inman et al. |
| 8,452,421 B2 | 5/2013 | Thenuwara et al. |
| 8,504,138 B1 | 8/2013 | Pivonka et al. |
| 8,538,523 B2 | 9/2013 | Sommer et al. |
| 8,538,541 B2 | 9/2013 | Milojevic et al. |
| 8,620,435 B2 | 12/2013 | Rooney et al. |
| 8,626,297 B2 | 1/2014 | Jaax et al. |
| 8,626,314 B2 | 1/2014 | Swoyer et al. |
| 8,634,928 B1 | 1/2014 | O'Driscoll et al. |
| 8,649,842 B2 | 2/2014 | Atalar et al. |
| 8,655,451 B2 | 2/2014 | Klosterman et al. |
| 8,706,240 B2 | 4/2014 | Bradley et al. |
| 8,718,781 B2 | 5/2014 | Alataris et al. |
| 8,774,927 B2 | 7/2014 | Deridder |
| 8,798,773 B2 | 8/2014 | Mashiach |
| 8,874,217 B2 | 10/2014 | Alataris et al. |
| 8,880,177 B2 | 11/2014 | Alataris et al. |
| 8,886,327 B2 | 11/2014 | Alataris et al. |
| 8,886,328 B2 | 11/2014 | Alataris et al. |
| 8,897,870 B2 | 11/2014 | De Ridder |
| 8,903,502 B2 | 12/2014 | Perryman et al. |
| 8,934,981 B2 | 1/2015 | De Ridder |
| 8,954,165 B2 | 2/2015 | Sharma et al. |
| 8,972,502 B2 | 3/2015 | Beslic et al. |
| 9,031,664 B2 | 5/2015 | Trier |
| 9,044,612 B2 | 6/2015 | Mashiach et al. |
| 9,061,151 B2 | 6/2015 | Mashiach et al. |
| 9,144,681 B2 | 9/2015 | Decre et al. |
| 9,220,897 B2 | 12/2015 | Perryman et al. |
| 9,254,393 B2 | 2/2016 | Perryman et al. |
| 9,403,020 B2 | 8/2016 | Wingeier |
| 9,433,750 B2 | 9/2016 | Pivonka et al. |
| 9,452,288 B2 | 9/2016 | Whitehurst et al. |
| 9,462,398 B2 | 10/2016 | Deridder |
| 9,463,318 B2 | 10/2016 | Mashiach |
| 9,555,248 B2 | 1/2017 | De Ridder |
| 9,555,257 B2 | 1/2017 | Mashiach et al. |
| 9,585,642 B2 | 3/2017 | Dinsmoor et al. |
| 9,623,245 B2 | 4/2017 | King et al. |
| 9,623,253 B2 | 4/2017 | Perryman et al. |
| 9,643,010 B2 | 5/2017 | Ranu |
| 9,656,077 B2 | 5/2017 | De Ridder |
| 9,656,085 B2 | 5/2017 | Moffitt et al. |
| 9,656,089 B2 | 5/2017 | Yip et al. |
| 9,707,406 B1 | 7/2017 | Dellamano et al. |
| 9,717,921 B2 | 8/2017 | Perryman et al. |
| 9,731,140 B1 | 8/2017 | Perryman et al. |
| 9,764,135 B2 | 9/2017 | De Ridder |
| 9,770,592 B2 | 9/2017 | Lin et al. |
| 9,789,314 B2 | 10/2017 | Perryman et al. |
| 9,789,321 B2 | 10/2017 | Dixit et al. |
| 9,826,963 B2 | 11/2017 | Scott et al. |
| 9,833,629 B2 | 12/2017 | Dellamano et al. |
| 9,913,975 B2 | 3/2018 | Carbunaru et al. |
| 9,993,646 B2 | 6/2018 | Parramon et al. |
| 10,004,635 B2 | 6/2018 | Kahook |
| 10,016,603 B2 | 7/2018 | Sachs et al. |
| 10,016,608 B2 | 7/2018 | Peterson et al. |
| 10,016,615 B2 | 7/2018 | Simon et al. |
| 10,016,627 B2 | 7/2018 | Viitala et al. |
| 10,022,549 B2 | 7/2018 | Dellamano et al. |
| 10,022,552 B2 | 7/2018 | Stahler et al. |
| 10,035,017 B2 | 7/2018 | Thakkar et al. |
| 10,035,020 B2 | 7/2018 | Wang et al. |
| 10,052,481 B2 | 8/2018 | McClure et al. |
| 10,076,668 B2 | 9/2018 | De Ridder |
| 10,086,201 B2 | 10/2018 | Chang et al. |
| 10,092,758 B2 | 10/2018 | De Ridder |
| 10,149,976 B1 | 12/2018 | Andresen et al. |
| 10,238,872 B2 | 3/2019 | Pivonka et al. |
| 10,238,874 B2 | 3/2019 | Perryman et al. |
| 10,245,436 B2 | 4/2019 | Perryman et al. |
| 10,272,239 B1 | 4/2019 | Andresen et al. |
| 10,315,039 B2 | 6/2019 | Perryman et al. |
| 10,320,232 B2 | 6/2019 | Pivonka et al. |
| 10,328,265 B2 | 6/2019 | Moffitt et al. |
| 10,335,596 B2 | 7/2019 | Yakovlev et al. |
| 10,411,760 B2 | 9/2019 | Yakovlev et al. |
| 10,420,947 B2 | 9/2019 | Perryman et al. |
| 10,471,262 B2 | 11/2019 | Perryman et al. |
| 10,644,539 B2 | 5/2020 | Pivonka et al. |
| 10,849,643 B2 | 12/2020 | Castillo et al. |
| 10,898,719 B2 | 1/2021 | Pivonka et al. |
| 10,967,183 B2 | 4/2021 | Yakovlev et al. |

(56) References Cited

U.S. PATENT DOCUMENTS

| | | |
|---|---|---|
| 11,018,721 B2 | 5/2021 | Yakovlev et al. |
| 11,090,491 B2 | 8/2021 | Mishra et al. |
| 11,097,096 B2 | 8/2021 | Linden et al. |
| 11,133,709 B2 | 8/2021 | Linden |
| 11,160,980 B2 | 11/2021 | Mishra et al. |
| 11,318,315 B2 | 5/2022 | Hartley et al. |
| 11,331,493 B2 | 5/2022 | Pivonka et al. |
| 11,451,265 B2 | 9/2022 | Yakovlev et al. |
| 11,511,121 B2 | 11/2022 | Sit |
| 11,633,151 B2 | 4/2023 | Pivonka et al. |
| 2002/0014039 A1 | 2/2002 | Merlet |
| 2002/0140399 A1 | 10/2002 | Echarri et al. |
| 2003/0055406 A1 | 3/2003 | Lebel et al. |
| 2004/0059392 A1 | 3/2004 | Parramon et al. |
| 2004/0106954 A1 | 6/2004 | Whitehurst et al. |
| 2004/0215287 A1 | 10/2004 | Swoyer et al. |
| 2005/0043765 A1 | 2/2005 | Williams et al. |
| 2005/0151696 A1 | 7/2005 | Govari |
| 2005/0245989 A1 | 11/2005 | Davis |
| 2005/0278000 A1 | 12/2005 | Strother et al. |
| 2005/0288596 A1 | 12/2005 | Eigler et al. |
| 2006/0004429 A1 | 1/2006 | Mrva |
| 2006/0074450 A1 | 4/2006 | Boveja et al. |
| 2006/0074458 A1 | 4/2006 | Imran |
| 2006/0095078 A1 | 5/2006 | Tronnes |
| 2006/0122653 A1 | 6/2006 | Bradley et al. |
| 2006/0149330 A1 | 7/2006 | Mann et al. |
| 2006/0224225 A1 | 10/2006 | Ransbury et al. |
| 2007/0032734 A1 | 2/2007 | Najafi |
| 2007/0049986 A1 | 3/2007 | Imran |
| 2007/0142874 A1 | 6/2007 | John |
| 2007/0156205 A1 | 7/2007 | Larson et al. |
| 2007/0270928 A1 | 11/2007 | Erlebacher |
| 2007/0288076 A1 | 12/2007 | Bulkes et al. |
| 2008/0045989 A1 | 2/2008 | Welborn et al. |
| 2008/0103569 A1 | 5/2008 | Gerber |
| 2008/0103578 A1 | 5/2008 | Gerber |
| 2008/0132981 A1 | 6/2008 | Gerber |
| 2008/0146871 A1 | 6/2008 | Arneson et al. |
| 2008/0161803 A1 | 7/2008 | Oral et al. |
| 2008/0269591 A1 | 10/2008 | Halperin et al. |
| 2008/0300654 A1 | 12/2008 | Lambert et al. |
| 2008/0300660 A1 | 12/2008 | John |
| 2009/0082835 A1 | 3/2009 | Jaax et al. |
| 2009/0088817 A1 | 4/2009 | Starkebaum et al. |
| 2009/0105782 A1 | 4/2009 | Mickle et al. |
| 2009/0112282 A1 | 4/2009 | Kast et al. |
| 2009/0171408 A1 | 7/2009 | Solem |
| 2009/0187230 A1 | 7/2009 | Dilorenzo |
| 2009/0204170 A1 | 8/2009 | Hastings et al. |
| 2009/0275956 A1 | 11/2009 | Burnes et al. |
| 2009/0281597 A1 | 11/2009 | Parramon et al. |
| 2010/0036454 A1 | 2/2010 | Bennett et al. |
| 2010/0082087 A1 | 4/2010 | Silipo et al. |
| 2010/0125312 A1 | 5/2010 | Stevenson et al. |
| 2010/0161002 A1 | 6/2010 | Aghassian et al. |
| 2010/0168817 A1 | 7/2010 | Yamamoto et al. |
| 2010/0249888 A1 | 9/2010 | Glenn et al. |
| 2010/0274314 A1 | 10/2010 | Alataris et al. |
| 2010/0274316 A1 | 10/2010 | Alataris et al. |
| 2011/0034886 A1 | 2/2011 | Elbe et al. |
| 2011/0054583 A1* | 3/2011 | Litt ................ A61N 1/0553 |
| | | 600/377 |
| 2011/0093032 A1 | 4/2011 | Boggs, II et al. |
| 2011/0106214 A1 | 5/2011 | Carbunaru et al. |
| 2011/0137378 A1 | 6/2011 | Klosterman et al. |
| 2011/0172737 A1 | 7/2011 | Davis et al. |
| 2011/0184337 A1 | 7/2011 | Evans et al. |
| 2011/0190849 A1 | 8/2011 | Faltys et al. |
| 2011/0257707 A1 | 10/2011 | Kothandaraman |
| 2011/0276110 A1 | 11/2011 | Whitehurst et al. |
| 2011/0301670 A1 | 12/2011 | Gross et al. |
| 2011/0301687 A1 | 12/2011 | Gross |
| 2011/0307032 A1 | 12/2011 | Goetz et al. |
| 2012/0004708 A1 | 1/2012 | Chen et al. |
| 2012/0004709 A1 | 1/2012 | Chen et al. |
| 2012/0012630 A1 | 1/2012 | Lui |
| 2012/0041508 A1 | 2/2012 | Rousso et al. |
| 2012/0197352 A1 | 8/2012 | Carbunaru et al. |
| 2012/0221074 A1 | 8/2012 | Funderburk et al. |
| 2012/0283800 A1 | 11/2012 | Perryman et al. |
| 2012/0296329 A1 | 11/2012 | Ng |
| 2012/0296444 A1 | 11/2012 | Greenberg et al. |
| 2013/0004925 A1 | 1/2013 | Labbe et al. |
| 2013/0012866 A1 | 1/2013 | Deem et al. |
| 2013/0023943 A1 | 1/2013 | Parramon et al. |
| 2013/0053767 A1 | 2/2013 | Pivonka et al. |
| 2013/0079861 A1 | 3/2013 | Reinert et al. |
| 2013/0096650 A1 | 4/2013 | Aghassian |
| 2013/0197609 A1 | 8/2013 | Moore et al. |
| 2013/0204321 A1 | 8/2013 | Alataris et al. |
| 2013/0211469 A1 | 8/2013 | Lamont et al. |
| 2013/0215979 A1 | 8/2013 | Yakovlev et al. |
| 2013/0261703 A1 | 10/2013 | Chow et al. |
| 2013/0310706 A1 | 11/2013 | Stone et al. |
| 2013/0310901 A1 | 11/2013 | Perryman et al. |
| 2013/0331638 A1 | 12/2013 | Cameron |
| 2014/0025140 A1 | 1/2014 | Lui |
| 2014/0046413 A1 | 2/2014 | Kane et al. |
| 2014/0094876 A1 | 4/2014 | Wingier |
| 2014/0100636 A1 | 4/2014 | Mashiach |
| 2014/0107709 A1* | 4/2014 | Schmitz ............ A61F 2/4611 |
| | | 606/279 |
| 2014/0142507 A1 | 5/2014 | Armes |
| 2014/0163580 A1* | 6/2014 | Tischendorf ......... A61N 1/0551 |
| | | 606/129 |
| 2014/0163638 A1 | 6/2014 | Marnfeldt |
| 2014/0163646 A1 | 6/2014 | Tischendorf et al. |
| 2014/0172047 A1 | 6/2014 | Spitaels et al. |
| 2014/0203823 A1 | 7/2014 | Joshi et al. |
| 2014/0222106 A1 | 8/2014 | Sharma et al. |
| 2014/0275847 A1 | 9/2014 | Perryman et al. |
| 2014/0277282 A1 | 9/2014 | Jaax |
| 2014/0288393 A1 | 9/2014 | Grevious et al. |
| 2014/0304773 A1 | 10/2014 | Woods et al. |
| 2014/0336727 A1 | 11/2014 | Perryman et al. |
| 2014/0346078 A1* | 11/2014 | Chang ................ A45C 11/00 |
| | | 206/521 |
| 2014/0371515 A1* | 12/2014 | John .................... A61N 1/3605 |
| | | 600/13 |
| 2015/0018728 A1 | 1/2015 | Gross et al. |
| 2015/0035378 A1 | 2/2015 | Calhoun et al. |
| 2015/0100110 A1 | 4/2015 | Towe et al. |
| 2015/0321000 A1 | 11/2015 | Rosenbluth et al. |
| 2015/0321002 A1 | 11/2015 | Khalil et al. |
| 2015/0335285 A1 | 11/2015 | Poon et al. |
| 2016/0023022 A1 | 1/2016 | Zarins et al. |
| 2016/0030666 A1* | 2/2016 | Lozano ............... A61N 1/0534 |
| | | 604/500 |
| 2016/0106994 A1 | 4/2016 | Crosby et al. |
| 2016/0113671 A1 | 4/2016 | Berger et al. |
| 2016/0136438 A1 | 5/2016 | Perryman et al. |
| 2016/0136443 A1* | 5/2016 | Grandhe ............. G16H 20/40 |
| | | 607/60 |
| 2016/0199658 A1 | 7/2016 | Nassif et al. |
| 2016/0218433 A1 | 7/2016 | Nghiem et al. |
| 2016/0331956 A1 | 11/2016 | Yakovlev et al. |
| 2016/0375237 A1* | 12/2016 | Hahn ................... A61N 1/05 |
| | | 607/116 |
| 2017/0001003 A1 | 1/2017 | Pivonka et al. |
| 2017/0028199 A1 | 2/2017 | Roehrlein et al. |
| 2017/0050021 A1 | 2/2017 | Cosman, Sr. |
| 2017/0054324 A1 | 2/2017 | Pivonka et al. |
| 2017/0054332 A1 | 2/2017 | Pivonka et al. |
| 2017/0087353 A1 | 3/2017 | Thota et al. |
| 2017/0095667 A1 | 4/2017 | Yakovlev et al. |
| 2017/0165491 A9 | 6/2017 | De Ridder |
| 2017/0189683 A1 | 7/2017 | Perryman et al. |
| 2017/0197082 A1 | 7/2017 | Pang et al. |
| 2018/0028824 A1 | 2/2018 | Pivonka et al. |
| 2018/0056080 A1 | 3/2018 | Reinke et al. |
| 2018/0064944 A1 | 3/2018 | Grill et al. |
| 2018/0071512 A1 | 3/2018 | Feldman et al. |
| 2018/0071536 A1 | 3/2018 | Skelton et al. |

(56) References Cited

U.S. PATENT DOCUMENTS

| | | |
|---|---|---|
| 2018/0083668 A1 | 3/2018 | Yakovlev et al. |
| 2018/0085593 A1 | 3/2018 | Fayram et al. |
| 2018/0169423 A1 | 6/2018 | Perryman et al. |
| 2018/0236237 A1 | 8/2018 | Kent et al. |
| 2018/0243563 A1 | 8/2018 | Vallejo et al. |
| 2018/0256906 A1 | 9/2018 | Pivonka et al. |
| 2018/0326220 A1 | 11/2018 | Kaula et al. |
| 2018/0333578 A1 | 11/2018 | Mock et al. |
| 2018/0368875 A1 | 12/2018 | Castillo et al. |
| 2019/0001139 A1 | 1/2019 | Mishra et al. |
| 2019/0008556 A1 | 1/2019 | Perryman et al. |
| 2019/0009097 A1 | 1/2019 | Hartley et al. |
| 2019/0143124 A1 | 5/2019 | Perryman et al. |
| 2019/0247198 A1 | 8/2019 | Zellmer et al. |
| 2019/0262610 A1 | 8/2019 | Kent et al. |
| 2019/0269913 A1 | 9/2019 | Pivonka et al. |
| 2019/0374776 A1 | 12/2019 | Mishra et al. |
| 2020/0101291 A1 | 4/2020 | Yakovlev et al. |
| 2020/0139138 A1 | 5/2020 | Sit et al. |
| 2020/0204209 A1 | 6/2020 | Yakovlev et al. |
| 2020/0222000 A1 | 7/2020 | Poon et al. |
| 2020/0306528 A1 | 10/2020 | Linden et al. |
| 2020/0398058 A1 | 12/2020 | Pivonka et al. |
| 2021/0099015 A1 | 4/2021 | Pivonka et al. |
| 2021/0196957 A1 | 7/2021 | Yakovlev et al. |
| 2021/0330981 A1 | 10/2021 | Mishra et al. |
| 2021/0399765 A1 | 12/2021 | Yakovlev et al. |
| 2022/0016103 A1 | 1/2022 | Baltcheva et al. |
| 2022/0016430 A1 | 1/2022 | Hartley et al. |
| 2022/0072300 A1 | 3/2022 | Yakovlev et al. |
| 2022/0080189 A1 | 3/2022 | Mishra et al. |
| 2022/0118251 A1 | 4/2022 | Buddha et al. |
| 2022/0134108 A1 | 5/2022 | Dinsmoor et al. |
| 2022/0176108 A1 | 6/2022 | Linden et al. |
| 2022/0176120 A1 | 6/2022 | Kulkarni et al. |
| 2022/0176133 A1 | 6/2022 | Buddha et al. |
| 2022/0218994 A1 | 7/2022 | Mishra et al. |
| 2022/0263346 A1 | 8/2022 | Pivonka et al. |
| 2023/0029600 A1 | 2/2023 | Pivonka |

FOREIGN PATENT DOCUMENTS

| | | |
|---|---|---|
| WO | WO-2007051146 A1 | 5/2007 |
| WO | WO-2007068284 A1 | 6/2007 |
| WO | WO-2008066556 A1 | 6/2008 |
| WO | WO-2010062517 A1 | 6/2010 |
| WO | WO-2013035092 A2 | 3/2013 |
| WO | WO-2014071079 A1 | 5/2014 |
| WO | WO-2014089299 A2 | 6/2014 |
| WO | WO-2014153124 A1 | 9/2014 |
| WO | WO-2014153219 A1 | 9/2014 |
| WO | WO-2014153228 A1 | 9/2014 |
| WO | WO-2014205129 A1 | 12/2014 |
| WO | WO-2015139053 A1 | 9/2015 |
| WO | WO-2015196164 | 12/2015 |
| WO | WO-2015196164 A2 | 12/2015 |
| WO | WO-2015196164 A3 | 2/2016 |
| WO | WO-2016028608 A1 | 2/2016 |
| WO | WO-2016113832 A1 | 7/2016 |
| WO | WO-2016127130 A1 | 8/2016 |
| WO | WO-2017044904 A1 | 3/2017 |
| WO | WO-2017142948 A1 | 8/2017 |
| WO | WO-2017165410 A1 | 9/2017 |
| WO | WO-2017205675 A1 | 11/2017 |
| WO | WO-2018017463 A1 | 1/2018 |
| WO | WO-2018023057 A1 | 2/2018 |
| WO | WO-2018126062 A1 | 7/2018 |
| WO | WO-2018144631 A1 | 8/2018 |
| WO | WO-2018156953 A1 | 8/2018 |
| WO | WO-2018208992 A1 | 11/2018 |
| WO | WO-2021003439 | 1/2021 |
| WO | WO-2021003439 A1 | 1/2021 |
| WO | WO-2021067873 | 4/2021 |
| WO | WO-2021067873 A1 | 4/2021 |
| WO | WO-2021/133947 | 7/2021 |
| WO | WO-2021133947 A1 | 7/2021 |
| WO | WO-2021262762 A1 | 12/2021 |
| WO | WO-2022047077 A1 | 3/2022 |
| WO | WO-2022103774 A1 | 5/2022 |

OTHER PUBLICATIONS

EP17831624.5 Extended Search Report dated Feb. 20, 2020.
"Search Report EP3253441 dated Jul. 5, 2018".
EP15809379.9 European Search Report dated Mar. 9, 2018.
European Search Report dated Oct. 12, 2017 for European Patent Application No. 15761577.4.
European Search Report dated Dec. 6, 2016 for European Application No. 14813206.1.
International Search Report and Written Opinion dated Apr. 14, 2016 for International Patent Application No. PCT/US2016/016888.
International search report and written opinion dated Jun. 24, 2015 for PCT/US2015/020808.
International search report and written opinion dated Dec. 18, 2015 for PCT/US2015/036821.
Office Action dated Oct. 20, 2017 for U.S. Appl. No. 15/264,864.
PCT/US2017/034553 International Search Report and Written Opinion dated Oct. 10, 2017.
PCT/US2017/068803 International Search Report and Written Opinion dated Mar. 6, 2018.
U.S. Appl. No. 14/975,358 Office Action dated May 15, 2018.
Buhlmann, J. et al., "Modeling of a segmented electrode for desynchronizing deep brain stimulation" Frontiers in Neuroengineering (2011) vol. 4, Article 15, pp. 1-1-8.
Butson, C. et al., "Current steering to Control the vol. of Tissue Activated During Deep Brain Stimulation" Brain Stimul. (2008) (1): 7-15.
EP14813206 Examination Report dated Apr. 23, 2020. 2 pages.
European Search Report and Written Opinion in EP Application No. 13852295.8, dated May 12, 2016, 10 pages.
European Search Report and Written Opinion in EP Application No. 16845235.7, dated Apr. 24, 2019, 8 pages.
European Search Report and Written Opinion in EP Application No. 17770982.1, dated Sep. 26, 2019, 7 pages.
European Search Report and Written Opinion in EP Application No. 17831624.6, dated Feb. 20, 2020, 9 pages.
European Search Report and Written Opinion in EP Application No. 18756643.5, dated Dec. 3, 2020, 10 pages.
European Search Report and Written Opinion in EP Application No. 18797777.2, dated Jan. 14, 2021, 7 pages.
International Preliminary Report on Patentability for PCT/US2021/038545, dated Dec. 13, 2022, 6 pages.
International Search Report and Written Opinion for PCT/US2014/043023; dated Oct. 6, 2014, 13 pages.
International Search Report and Written Opinion for PCT/US2016/051177, dated Nov. 10, 2016, 18 pages.
International Search Report and Written Opinion for PCT/US2017/023400, dated Mar. 6, 2018, 8 pages.
International Search Report and Written Opinion for PCT/US2018/019522, dated Jun. 15, 2018, 12 pages.
International Search Report and Written Opinion for PCT/US2018/031904, dated Jul. 26, 2018, 10 pages.
International Search Report and Written Opinion for PCT/US2020/040766, dated Oct. 6, 2020, 7 pages.
International Search Report and Written Opinion for PCT/US2020/054150, dated Jan. 6, 2021, 11 pages.
International Search Report and Written Opinion for PCT/US2020/066901, dated Mar. 15, 2021, 7 pages.
International Search Report and Written Opinion for PCT/US2021/038545, dated Mar. 15, 2021, 7 pages.
Non-Final Office Action dated Feb. 24, 2023, for U.S. Appl. No. 17/240,629, filed Apr. 26, 2021, 12 pages.
Quayle Action mailed on Apr. 12, 2023, for U.S. Appl. No. 17/487,535, filed Sep. 28, 2021, 7 pages.
U.S. Appl. No. 63/042,293, inventors Mishra; Lakshmi Narayan et al., filed Jun. 22, 2020, 101 pages.

(56) References Cited

OTHER PUBLICATIONS

U.S. Appl. No. 14/975,358 Office Action dated Dec. 5, 2019. 9 pages.
U.S. Appl. No. 14/975,358 Office Action dated Jul. 27, 2020. 12 pages.
U.S. Appl. No. 14/975,358 Office Action dated Nov. 2, 2020. 18 pages.
U.S. Appl. No. 14/975,358 Office Action dated Nov. 20, 2018. 9 pages.
U.S. Appl. No. 16/672,921 Notice of Allowance dated Apr. 23, 2021. 7 pages.
U.S. Appl. No. 16/672,921 Office Action dated Feb. 16, 2021. 11 pages.
U.S. Appl. No. 16/672,921 Office Action dated Mar. 22, 2021. 12 pages.
Yakovlev, Anatoly et al., "Implantable Biomedical Devices: Wireless powering and communication," IEEE Communications Magazine, IEEE Service Center, vol. 50, No. 4, Apr. 1, 2012, pp. 152-159.

* cited by examiner

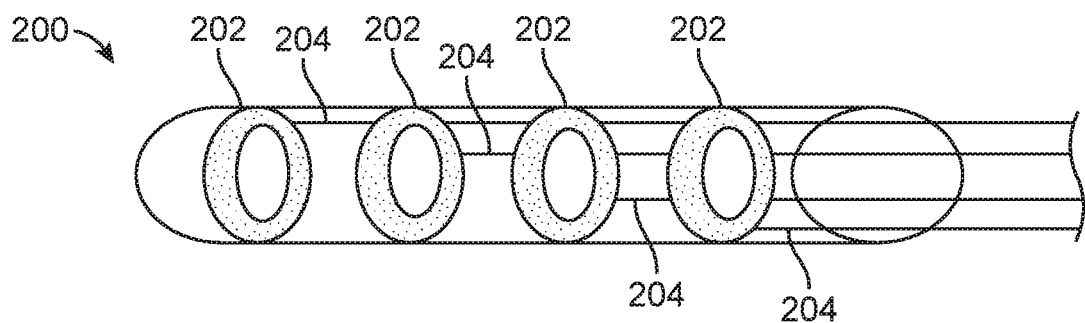
FIG. 10A
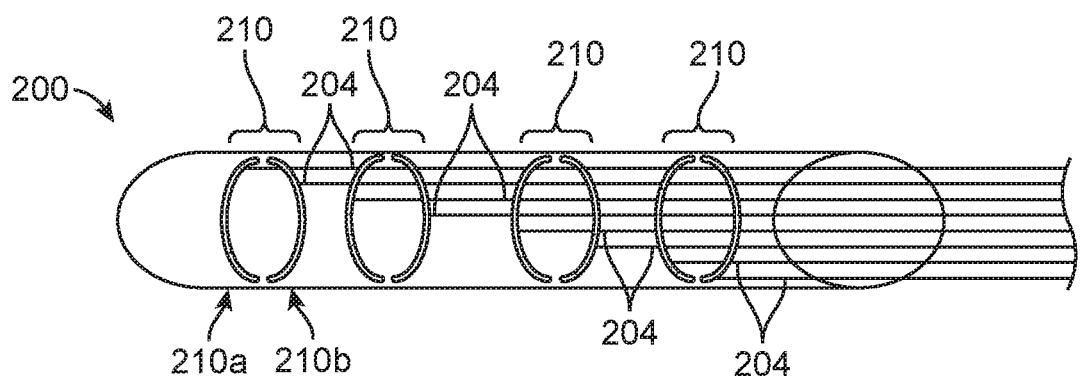
FIG. 10B
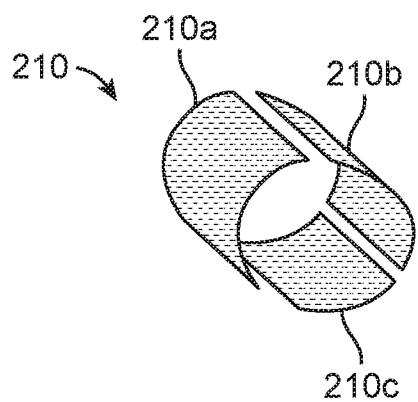 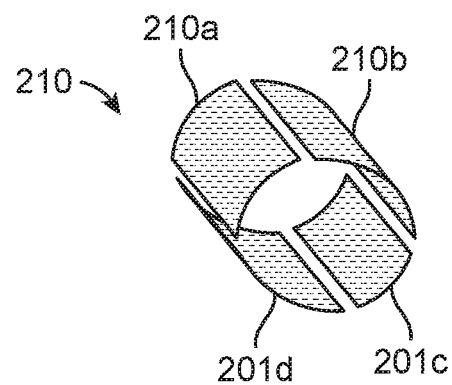
FIG. 11             FIG. 12

METHODS AND SYSTEMS FOR TREATING PELVIC DISORDERS AND PAIN CONDITIONS

CROSS REFERENCE

This application is a continuation of PCT Application No. PCT/US17/42351, filed Jul. 17, 2017, which claims priority to U.S. Provisional Patent Application Ser. No. 62/363,742, filed Jul. 18, 2016, the content of which is incorporated herein by reference in its entirety for all purposes.

RELATED APPLICATIONS

This application is related to: U.S. patent application Ser. No. 14/424,303, titled "Wireless Implantable Sensing Devices", filed Feb. 26, 2015; U.S. patent application Ser. No. 14/975,358, titled "Method and Apparatus for Minimally Invasive Implantable Modulators", filed Dec. 18, 2015; U.S. patent application Ser. No. 15/264,864, titled "Method and Apparatus for Versatile Minimally Invasive Neuromodulators", filed Sep. 14, 2016; U.S. patent application Ser. No. 15/385,729, titled "Method and Apparatus for Neuromodulation Treatments of Pain and Other Conditions", filed Dec. 20, 2016; International PCT Patent Application Ser. No. PCT/US2016/016888, titled "Medical Apparatus Including an Implantable System and an External System", filed Feb. 5, 2016; International PCT Patent Application Ser. No. PCT/US2016/051177, titled "Apparatus for Peripheral or Spinal Stimulation", filed Sep. 9, 2016; International PCT Patent Application Ser. No. PCT/US2017/017978, titled "Apparatus with Enhanced Stimulation Waveforms", filed Feb. 15, 2017; International PCT Patent Application Ser. No. PCT/US2017/023400, titled "Devices and Methods for Positioning External Devices in Relation to Implanted Devices", filed Mar. 21, 2017; International PCT Patent Application Serial Number PCT/US2017/034553, titled "Methods and Systems for Insertion and Fixation of Implantable Devices", filed May 25, 2017; U.S. Provisional Patent Application Ser. No. 62/441,056, titled "Stimulation Apparatus", filed Dec. 30, 2016; U.S. Provisional Patent Application Ser. No. 62/463,328, titled "Apparatus with Sequentially Implanted Stimulators", filed Feb. 24, 2017; and U.S. Provisional Patent Application Ser. No. 62/503,772, titled "Stimulation Apparatus", filed May 9, 2017; the content of each of which is incorporated herein by reference in its entirety for all purposes.

FIELD OF THE INVENTION

The present invention relates generally to medical apparatus for a patient, and in particular, apparatus that deliver enhanced stimulation to effectively deliver a therapy while avoiding undesired effects.

BACKGROUND OF THE INVENTION

Implantable devices that treat a patient and/or record patient data are known. For example, implants that deliver energy such as electrical energy, or deliver agents such as pharmaceutical agents are commercially available. Implantable electrical stimulators can be used to pace or defibrillate the heart, as well as modulate nerve tissue (e.g. to treat pain). Most implants are relatively large devices with batteries and long conduits, such as implantable leads configured to deliver electrical energy or implantable tubes (i.e. catheters) to deliver an agent. These implants require a fairly invasive implantation procedure, and periodic battery replacement, which requires additional surgery. The large sizes of these devices and their high costs have prevented their use in a variety of applications.

Nerve stimulation treatments have shown increasing promise recently, showing potential in the treatment of many chronic diseases including drug-resistant hypertension, motility disorders in the intestinal system, metabolic disorders arising from diabetes and obesity, and both chronic and acute pain conditions among others. Many of these implantable device configurations have not been developed effectively because of the lack of miniaturization and power efficiency, in addition to other limitations.

There is a need for apparatus, systems, devices and methods that provide one or more implantable devices and are designed to provide enhanced treatment of pain and other enhanced benefits.

SUMMARY OF THE INVENTION

The present inventions relate to neuromodulation methods, systems, devices and accessories for the treatment of pelvic disorders and acute and chronic pain conditions, as well as other conditions or disorders. Pelvic disorders may include fecal incontinence; overactive bladder; urinary urgency; urinary incontinence; urge frequency; non-obstructive urinary retention; female sexual dysfunction; constipation; diarrhea; irritable bowel syndrome; colitis; detrusor instability; detrusor dysfunction; spastic bladder; neurogenic bladder; detrusor sphincter dyssynergia; detrusor hyperreflexia; detrusor areflexia; pelvic pain; painful bladder syndrome; Hunner's ulcers or lesions; interstitial cystitis; pelvic floor dysfunction; endometriosis; vulvodynia; dyspareunia; pelvic adhesions; abdominal adhesions; pelvic girdle pain; pudendal nerve entrapment; pudendal neuralgia; dysmenorrhea; Müllerian abnormalities; pelvic inflammatory disease; ovarian cysts; ovarian torsion; Loin pain hematuria syndrome; proctitis; prostatitis; prostadynia; post-abdominal surgical pain; post-pelvic surgical pain; hernia pain; post-hernia surgical pain; anal pain; rectal pain; perineal pain; groin pain; vulvar pain; vaginal pain; clitoral pain; colitis; and combinations of one or more of the these.

Chronic pain may include but is not limited to lower back and leg pain, migraine headaches, neuropathic pain, pain associated with herniated discs, muscle spasm or pinched nerve anywhere in the body, foot pain such as plantar fascitis, plantar fibroma, neuromas, neuritis, bursitis, and ingrown toenails. Also addressed may be pain associated with malignant tumors. Acute pain may include but is not limited to postsurgical pain such as pain associated with thoracotomy or inguinal hernia repair, or pain associated with procedures where an epidural block is used. This may be particularly and uniquely applicable in pregnancy to preliminarily disable the sensory nerves without the use of drugs and prior to delivery to avoid the potential for missing the window of time where an epidural can be administered. Such neuromodulation involves precise, controlled modulation of specific nerves or tissues to induce physiological effects for therapies. In some instances, modulation is accomplished with a minimally invasive neuromodulation system that can target specific nerves with configurable modulation parameters and/or sensors for diagnostics or adaptations to the therapy. The neuromodulation system includes at least one implantable device, that serves as one or more modulators. In some embodiments, the implantable device is passive, wherein it receives power from at least one external device that communicates or interfaces with the implantable device. In other embodiments, the implantable device is active and includes a battery.

The one or more implantable modulators provides modulating energy that directly or indirectly effects the composition or behavior of the targeted nerve or tissue. Specific parameters of the modulating energy may be chosen for different treatment modalities. The one or more modulators are positioned in, on, around, or in the proximity of nerves or tissues to be influenced and are typically delivered in a minimally invasive manner through an introducer with anatomical guidance. The one or more modulators may be directly or indirectly attached to the nerves through a variety of methods based on the specific type of nerve or tissue as well as the intended therapy. Close proximity to nerves can reduce energy requirements and can eliminate unwanted stimulation of surrounding nerve tissue. The one or more modulators may be placed at a multitude of locations and configured with multiple parameters to increase the configurability of the treatment. For example, high frequency stimulation can block signals, while low frequency stimulation can mask symptoms. Multiple nerves can be stimulated in coordination, which may be provided with multiple modulators or interfaces. Real-time information, which may be provided by sensors in the devices or apparatuses, can further enhance the efficacy of therapy and may be applied for guided placement of an interface.

According to a first aspect of the invention, a stimulation system comprises: an implantable lead having a proximal end and a distal end, and at least one electrode along its distal end; an implantable neuromodulation stimulator disposed along the proximal end of the implantable lead; and an external device comprising a battery, a transmitter, and an antenna. The implantable lead can be integral to the implantable neuromodulation stimulator.

In some embodiments, the external device transmits power and/or data to the implantable neuromodulation stimulator. The external device can transmit power and data to the implantable neuromodulation stimulator.

In some embodiments, the external device comprises an interface and/or an autonomous control algorithm to control therapy and/or monitor therapy effectiveness.

In some embodiments, the implantable device is configured to be implanted in the patient for a time period selected from the group consisting of: less than 2 days; less than 1 week; less than 1 month; at least 1 month; at least 3 months; at least 6 months; and combinations thereof.

In some embodiments, the implantable neuromodulation stimulator comprises non-adjustable functional parameters.

In some embodiments, the external device comprises a housing that is hermetically or non-hermetically sealed.

In some embodiments, the external device comprises a housing configured to provide a water-resistant barrier.

In some embodiments, the external device comprises at least one encapsulant configured to reduce moisture ingress.

In some embodiments, the implantable lead comprises a paddle lead including a cylindrical flexible shaft and a paddle shaped distal end.

In some embodiments, the at least one electrode comprises two or more electrodes including longitudinal and lateral spans to cover concurrent stimulation sites. The at least one electrode comprises twelve independently programmable electrodes across three columns.

In some embodiments, the implantable lead comprises a length that correlates to the anatomical positioning of the device.

In some embodiments, the implantable neuromodulation stimulator is configured to provide bilateral stimulation and/or unilateral stimulation at multiple target locations. The multiple target locations can comprise multiple locations within multiple foramina.

In some embodiments, the external device is configured to gather information regarding: the implantable neuromodulation stimulator; the patient; and/or the patient's environment.

In some embodiments, the implantable neuromodulation stimulator comprises an implantable battery and an implantable antenna that comprises a printed circuit board (PCB) antenna. The implantable antenna can surround the implantable battery.

In some embodiments, the at least one electrode comprises at least one set of segmented electrodes. The at least one set of segmented electrodes can be configured to focus current delivery. The at least one set of segmented electrodes can comprise a first segment configured to provide stimulation energy and a second segment configured to record Evoked Compound Action Potentials (ECAPs). The system can be configured to determine the relative measure of the location of the implantable lead using the recorded ECAPs.

In some embodiments, the stimulation system further comprises a communication device configured to perform a function selected from the group consisting of: define the therapy to be delivered by the system; modify the therapy to be delivered by the system; run an algorithm to establish therapy modifications; and combinations thereof. The communication device can comprise a smart phone. The stimulation system can further comprise a charger and charger base, the communication device can transmit information to the charger base, the charger can receive the information from the charger base, and the charger can send the information to the implantable neuromodulator stimulator. The implantable neuromodulation stimulator can comprise an implantable battery, and the charger can be configured to collect battery statistics from the implantable neuromodulation stimulator during charging of the implantable battery. The charger can be configured to upload the battery statistics to a server via a wired and/or wireless link. The server can comprise a remote cloud server. The communication device can be configured to gather patient feedback, and the system can adjust the stimulation based on the gathered patient feedback. The stimulation adjustment can be further based on time of day information and/or activity information.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 10A is a schematic illustration of a distal end of a lead having ring electrodes.

FIG. 10B is a schematic illustration of a distal end of a lead having segmented electrodes.

FIG. 11 illustrates an embodiment of a segment electrode comprising three segments.

FIG. 12 illustrates an embodiment of a segmented electrode comprising four segments.

DETAILED DESCRIPTION OF THE INVENTION

Specific embodiments of the neuromodulation methods, systems, and devices for the treatment of acute and chronic pain conditions, pelvic disorders, as well as other conditions or disorders, will now be described with reference to the drawings. Nothing in this detailed description is intended to imply that any particular component, feature, or step is essential to the invention.

Passive and Active Neuromodulation Systems

Figure 1:
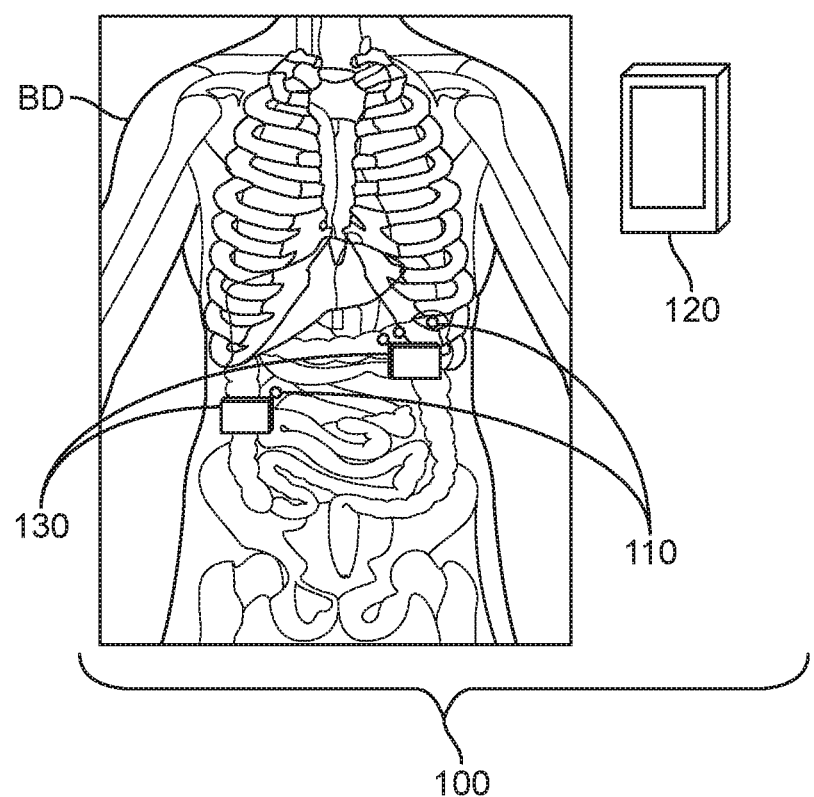
FIG. 1 schematically illustrates example external devices positioned outside the body wherein each external device interfaces with one or more implantable devices.

In some embodiments, neuromodulation is achieved with the use of at least one external device that interfaces with one or more permanently or temporarily implantable modulators. The at least one external device provides power and optionally controls the operation of the implantable modulator and/or gathers information regarding the implantable modulator and/or the patient. One or more of the external devices can also provide an interface for a patient or a clinician or an autonomous control algorithm to control the therapy and monitor its effectiveness. FIG. 1 schematically illustrates example external devices 130 positioned outside the body BD, wherein each external device 130 interfaces with one or more implanted modulators or other implanted devices, implantable devices 110 shown Each implantable device 110 can be configured to be implanted in the patient for a relatively short period of time (e.g. explanted within 2 days, within 1 week, or within 1 month of implantation), and/or for a relatively long period of time (e.g. implanted for at least 1 month, at least 3 months, or at least 6 months). In some instances, the elements of the overall system 100 can allow for miniaturized implantable devices 110 in the cm, mm and sub-mm size range. This miniaturization can be accomplished in part by the ability of the overall system 100 to utilize a variety of different antennas and an on-board intelligent power management system. The external device 130 may include components for power transfer, power storage (e.g. battery), battery management, data transfer, programmability, data management (including processing and visualization) and a user interface for clinicians and/or patients. The user interface could consist of button(s), a touchscreen display, knob(s), keyboard, keypad, display, microphone, light, speaker and/or other component configured for user input and/or user output. Optionally, some of these components can be disposed in a handheld interface 120, such as a programmer.

Figure 2:
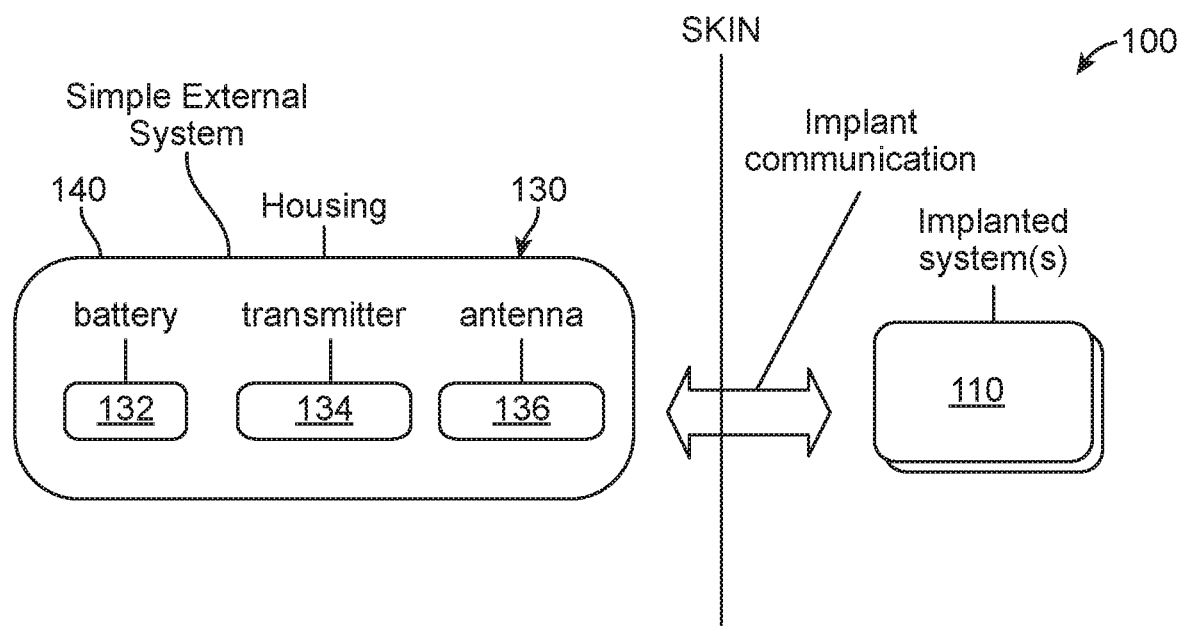
FIG. 2 schematically illustrates an example system comprising an implantable device and an external device.

FIG. 2 schematically illustrates an example system 100 comprising an implantable device 110 and a simple external device 130. Here, the external device 130 comprises a battery 132, a transmitter 134 and an antenna 136 for the purpose of exciting (e.g. providing power to) an implantable device 110 that has permanently established (e.g. non-adjustable) functional parameters (e.g. stimulation amplitudes, rates, duty cycles, contacts, etc.). Such a device 130 may be disposable (e.g. single use) or rechargeable. Such disposable embodiments may contain primary cell batteries (e.g. alkaline, lithium, Zn-Air) or no battery and rechargeable embodiments may contain rechargeable batteries (NiMH, lithium-ion, lithium-polymer) or chargeable/pre-charged supercaps. Rechargeable batteries may be removable or permanently integrated. In certain embodiments, such simple external devices 130 may be targeted to be single use, short term use or long term reusable. Since such external devices 130 are free of advanced complexity, they can be smaller in size and very robust. In some embodiments, the external device 130 includes a housing 140 which may be hermetically or non-hermetically sealed. In some instances, the housing 140 is waterproof or at least water resistant, such as to facilitate use by patients during activities such as swimming or working in unusually dirty areas or during particularly strenuous activities (e.g. playing sports).

Figure 3:
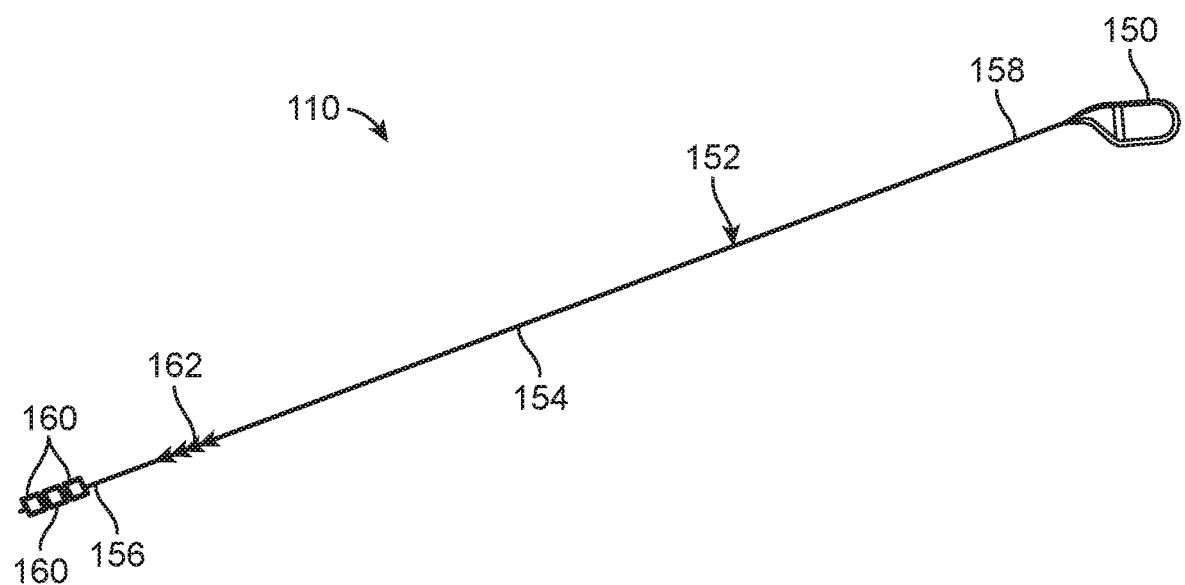
FIG. 3 illustrates an embodiment of a passive implantable device.
Figure 4:
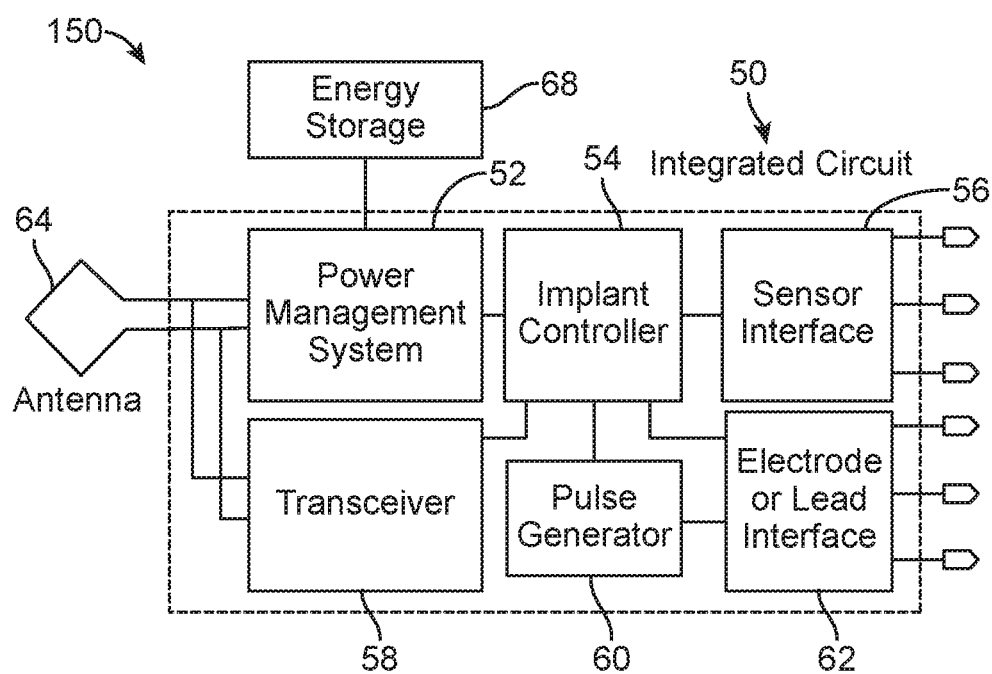
FIG. 4 illustrates example electronics within an implantable neuromodulation stimulator.

As mentioned, in some embodiments the implantable device 110 is "passive", wherein it receives power from at least one external device 130 that communicates or interfaces with the implantable device 110. FIGS. 3-4 illustrate embodiments of passive implantable devices 110. FIG. 3 is an illustration of an embodiment of an implantable device 110 comprising an implantable neuromodulation stimulator (INS) 150 which is integral with a lead 152. In this embodiment, the lead 152 comprises an axial lead having a cylindrical flexible shaft 154 comprising a distal end 156 and a proximal end 158. At least one electrode 160 is disposed along the distal end 156 and is positionable at a target location within the patient's body, such as in, on, around, or in the proximity of nerves or tissues to be influenced by the modulation energy. The one or more electrodes provide modulating energy that directly or indirectly effects the composition or behavior of the targeted nerve or tissue. In some embodiments, the implantable device 110 includes one or more anchors 162, such as tines, which extend from the shaft 154 and grip or provide friction against the surrounding tissue. Anchors 162 assist in maintaining position of the electrodes 160 at a desired target location. The INS 150 is disposed along the proximal end 158 of the shaft 154. Typically, the INS 150 includes electronics for the controlled delivery of stimulation which may include all or some of: passive power reception circuitry, battery, antenna, power supplies, printed circuit board or other electronic subassembly, and/or direct current blocking capacitors. FIG. 4 illustrates example electronics within the INS 150. In this embodiment, the INS 150 includes an integrated circuit 50 comprising a power management system 52, an implant controller 54, a sensor interface 56, a transceiver 58, a pulse generator 60 and an electrode or lead interface 62. The INS 150 also includes an antenna 64 and energy storage 68. Typically, the INS 150 also includes feedthroughs enabling electrical connection between the conductors of the lead 152 and the electronics inside a hermetic housing surrounding the INS 150. In other embodiments, a specifically hermetic housing may be replaced by encapsulants (e.g. polymers such as Urethane) to achieve moderate protection against moisture ingress suitable for some applications. Such an integrated lead system having a miniaturized INS 150 lends itself well to implantation by minimally invasive surgery.

Figure 5:
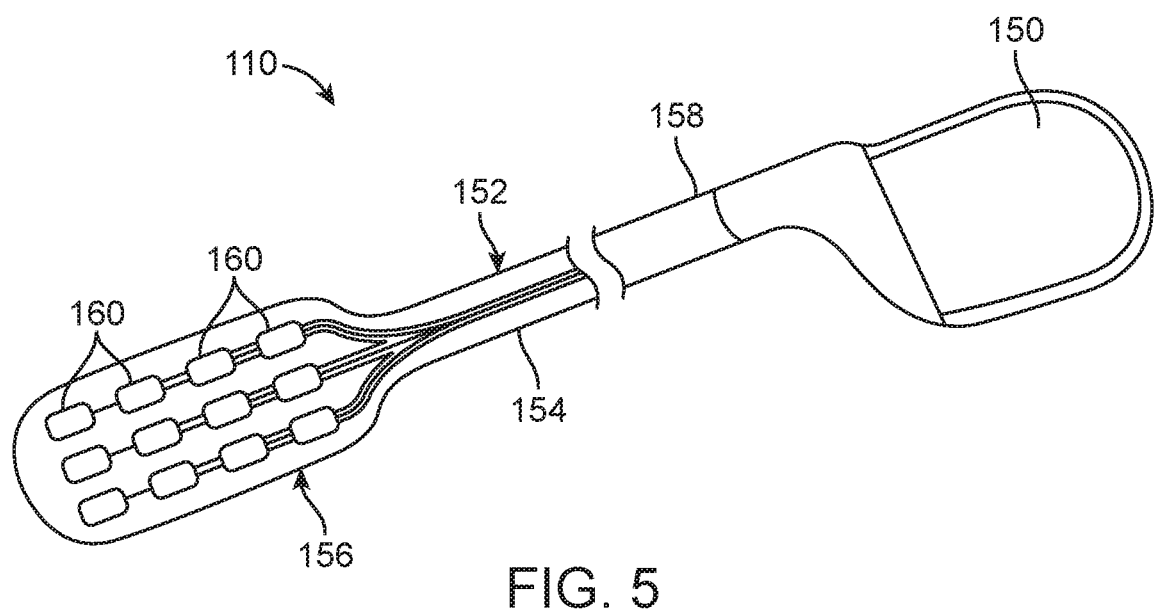
FIG. 5 illustrates an embodiment of a passive implantable device having a paddle shaped distal end.

FIG. 5 illustrates another embodiment of an implantable device 110 or modulator comprising an implantable neuromodulation stimulator (INS) 150 which is integral with a lead 152. In this embodiment, the lead 152 comprises a paddle lead having a cylindrical flexible shaft 154 and a paddle shaped distal end 156. At least one electrode 160 is disposed along the distal end 156 and is positionable at a target location within the patient's body, such as in, on, around, and/or in the proximity of nerves or tissues to be influenced by the modulation energy. In this embodiment, the distal end 156 includes a plurality of electrodes 160. The electrodes 160 can have longitudinal and lateral spans to cover concurrent stimulation sites. In this embodiment, the lead includes 12 independently programmable electrodes 160 across three columns. The one or more electrodes 160 provide modulating energy that directly and/or indirectly effects the composition or behavior of the targeted nerves or tissues. The INS 150 is disposed along the proximal end 158 of the shaft 154. The INS 150 typically includes electronics for the controlled delivery of stimulation which may include all or some of passive power reception circuitry, battery, antenna, power supplies, printed circuit board or other electronic subassembly, direct current blocking capacitors, such as is described hereabove in reference to FIG. 4.

Figure 6:
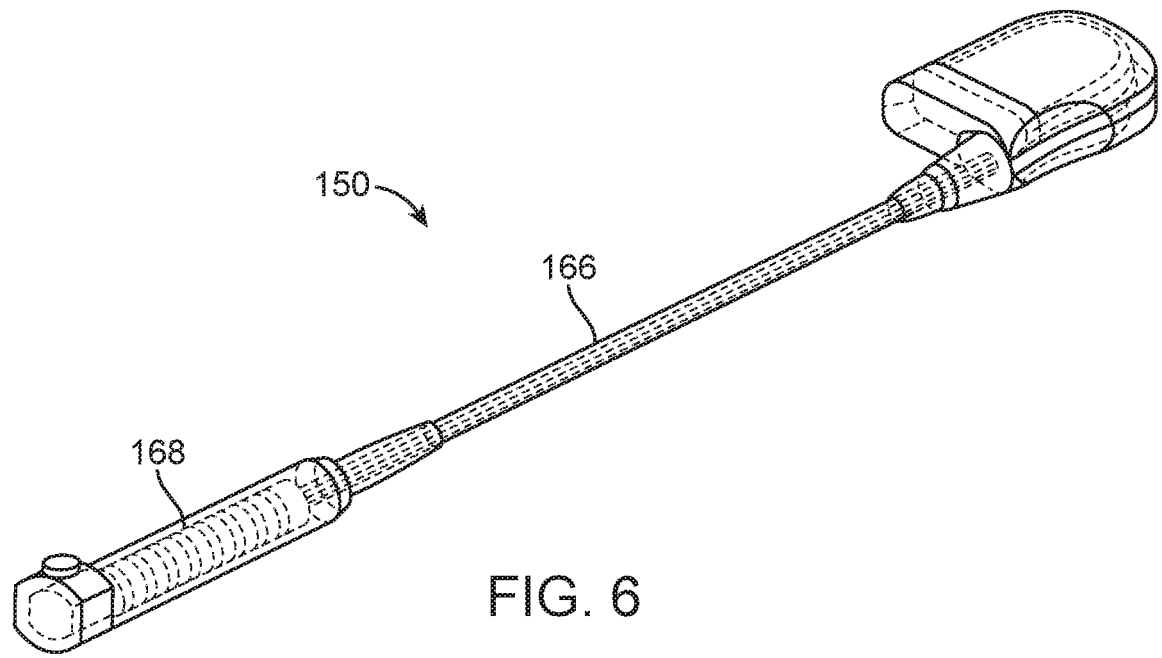
FIG. 6 illustrates an embodiment of a passive implantable device having an extension and connector.

FIG. 6 is an illustration of an embodiment of an INS 150 which is connectable with a proximal end 158 of a lead 152. In this embodiment, the INS 150 includes an extension 166 and a connector 168. The connector 168 is configured to receive the proximal end of the lead 152, which is insertable therein, so as to electrically connect the at least one electrode 160 with the pulse generator. Typically, the proximal end of the lead 152 has a contact for each electrode 160 on the lead 152, and is mateable with contacts within the connector 168. In most embodiments, the extension 166 is flexible and may have any suitable length applicable to the anatomical positioning of the implantable device 110. It may be appreciated that in some embodiments, the INS 150 includes more than one extensions 166 with associated connectors 168. Thus, the INS 150 may have one, two, three, four, five, six or more extensions 166 with associated connectors 168.

Figure 7:
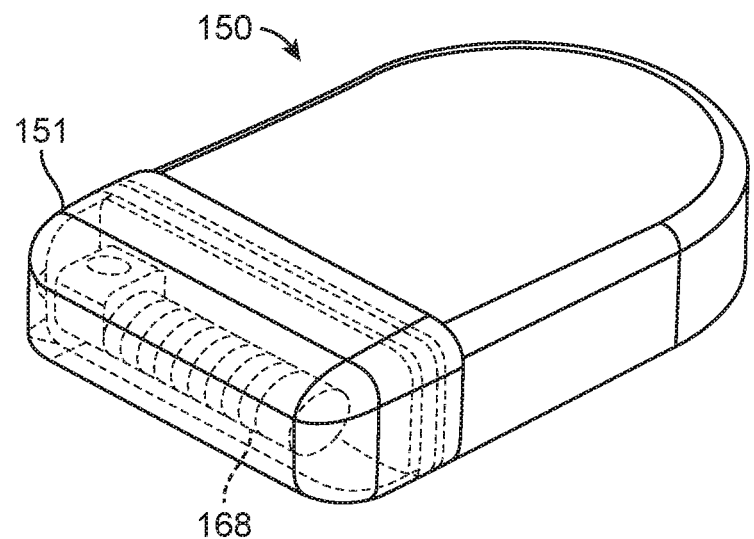
FIG. 7 provides a perspective view illustration of an embodiment of an INS having a header with a built in connector.

In some embodiments, the INS 150 does not include an extension 166. Rather, the connector 168 is built into a header 151 of the INS 150. FIG. 7 provides a perspective view illustration of an embodiment of an INS 150 having a header 151 with a built in connector 168. It may be appreciated that in some embodiments, the header 151 includes more than one connector 168. Thus, the INS 150 may have one, two, three, four, five, six or more connectors 168.

In either case, multiple connectors 168 can minimize the device size in a chosen axis. Likewise, multiple bifurcated lead integrated implantable devices 100 or multiple connectors 168 can allow bilateral stimulation and/or unilateral stimulation at multiple target locations, such as target stimulation located within multiple foramina.

Figure 8:
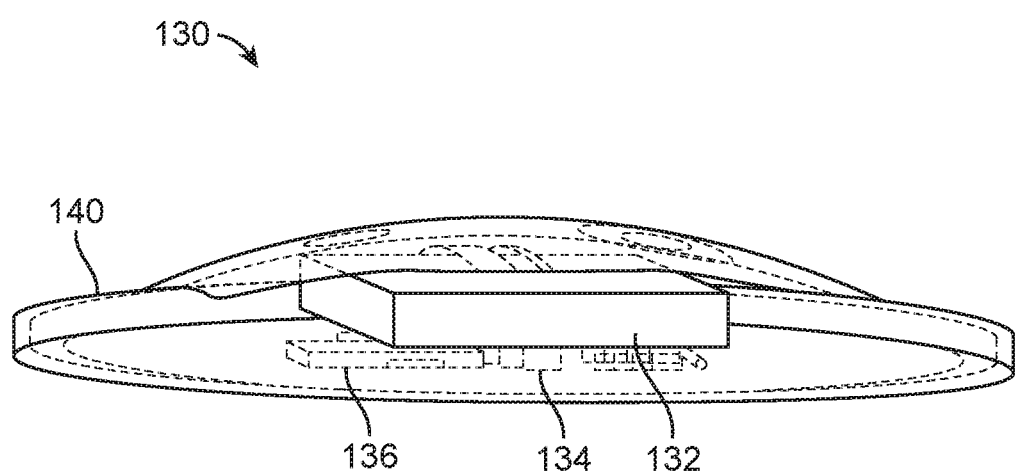
FIG. 8 illustrates an embodiment of an external device which communicates with an implantable device.

As mentioned, the passive implantable devices 110 are each paired with at least one external device 130. The at least one external device 130 provides power and optionally controls the operation of each implantable device 110, and/or gathers information regarding each implantable device 110, information regarding the patient, and/or information regarding the patient's environment. One or more of the external devices 130 can also provide an interface for a patient or a clinician to control the therapy and monitor its effectiveness. FIG. 8 illustrates an embodiment of an external device 130. Here, the external device 130 includes a battery 132 (such as a 250 mAh battery), transmitter 134 and antenna 136, among other elements, which are contained in a housing 140. In this embodiment, the external device 130 has been designed to make it amenable to be adhered to skin and placed over the implant site. Additionally or alternatively, the external device 130 can be worn with a belt or other patient-attachment device.

Figure 9:
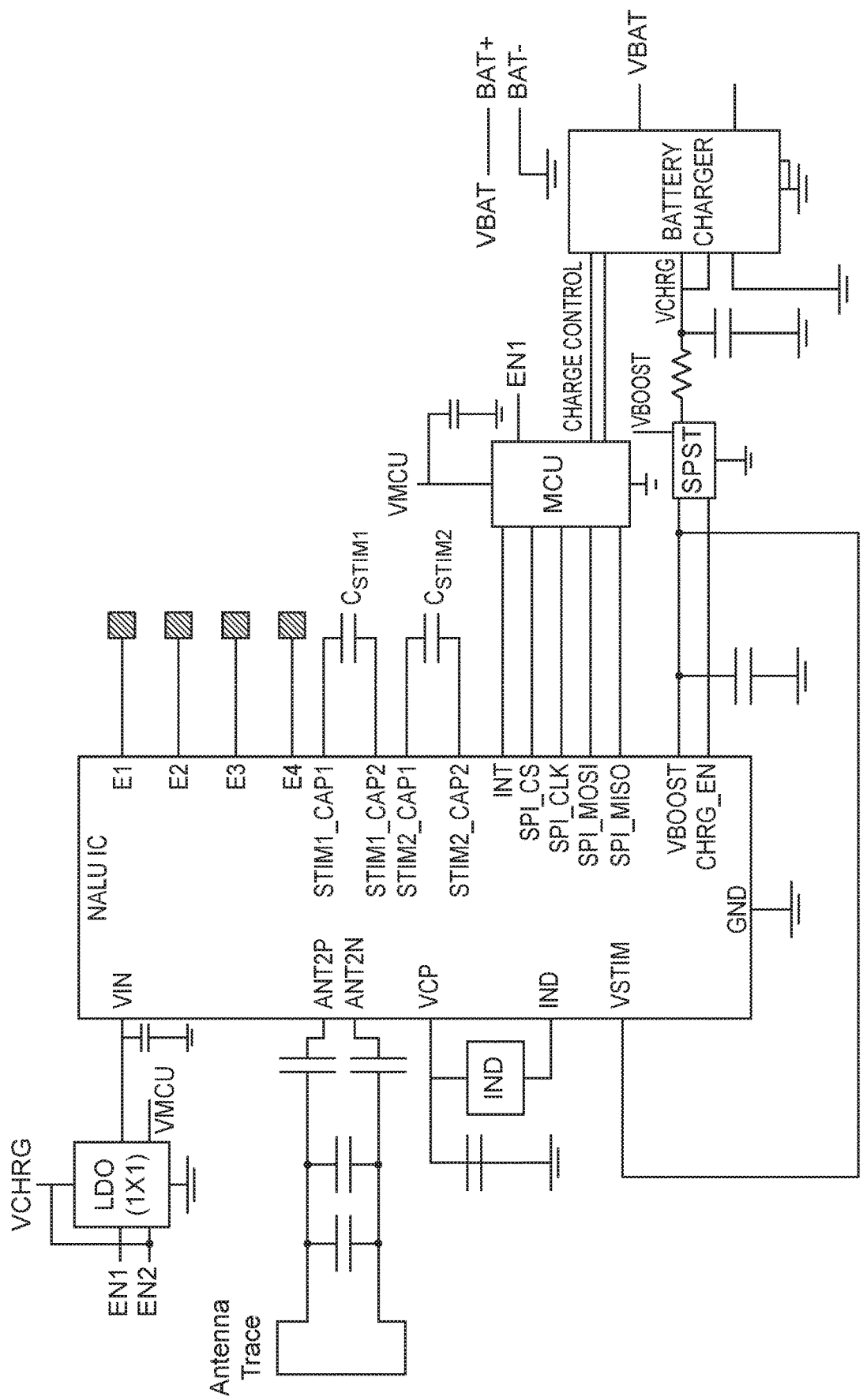
FIG. 9 provides a schematic block diagram of components of an embodiment of an implantable device which is active as opposed to passive.

In some embodiments, the implantable device 110 is active wherein it includes a power source, such as a battery. FIG. 9 provides a schematic block diagram of components of an embodiment of an implantable device 110 which is active. In this embodiment, the implantable device 110 includes a battery (e.g. a 50 mAh or 35 mAh battery), a printed circuit board assembly (PCBA), such as a PCBA implementing the circuit illustrated in FIG. 9, and a feedthrough with sufficient contacts positioned to be used across multiple therapeutic indications (e.g. pudental nerve versus sacral nerve or other location, each of which can require different quantity, size, orientation or pitch of contacts and/or connected electrodes). An antenna is implemented as a printed circuit board (PCB) antenna and surrounds the battery of the implantable device 110. This approach is an alternative to having a stand-alone antenna and efficiently uses available volumetric space. In this embodiment, the rest of the PCB has been "placed on its side" to further optimize the use of space. The antenna can also be used (with a companion chip) as part of a wireless communication system with a remote control. For instance, a Medical Implant Communication Service (MICS) communication IC (e.g. http://www.microsemi.com/products/ultra-low-power-wireless/implantable-medical-transceivers/zl70103) could be included in the system with a switch to select between the modes (e.g. a first mode in which power and/or data is transferred over a short range, and a second mode in which the MICS is used for long communication, such as using the above described remote control). Alternatively, a single frequency in the MICS band could be used for both functions and a single chip could implement both functions.

For any active implantable device 110, one of the key factors governing the longevity of use of the device is the battery. The loss of capacity of the battery as it is cycled eventually leads to an undesirably low capacity (e.g. too low a capacity for effective use). In some embodiments, the implantable device 110 will integrate a Li-Ion cell and manage the cell life carefully by manipulating the maximum charge voltage and minimum discharge voltage, and vary these parameters as the cell ages. For example, at the beginning of life, the charge to voltage (target battery voltage at the end of a charge cycle) may be set to 3.9V, and over the course of cycling be increased up to 4.0V, 4.1V, and/or 4.2V. Similarly, the minimum discharge voltage (the voltage at which the system will shut down or otherwise enter low power modes with potentially reduced functionality) can be decreased over time, such as to optimally maintain the required capacity from the cell.

Leads

Traditional neuromodulation leads comprise a relatively cylindrical geometry. The cylindrical leads typically have ring electrodes which extend around the perimeter of the lead. Such leads are forgiving in terms of the orientation of the leads with respect to the nerve but can be wasteful in terms of energy utilization for stimulation. Stimulation may not be directed entirely towards the target nerve and may result in recruitment of other neural tissue leading to adverse/uncomfortable stimulation. Such undesired stimulation may result in the patient either reducing stimulation current levels and/or not using the device—and either of these scenarios could result in poor outcomes.

An alternate approach is to segment the electrodes on the lead (e.g. into one or more sets of segmented electrodes as described herebelow). FIGS. 10A-10B are schematic illustrations of ring electrodes and segmented electrodes, respectively. In particular, FIG. 10A illustrates the distal end of a lead 200 having four ring electrodes 202 disposed along its length. Each ring electrode 202 has a conductive wire 204 attached thereto. The conductive wires 204 extend along the length of the lead 200 and connect with a pulse generator (e.g. an implantable device 100) to provide electrical signals to the associated electrode. FIG. 10B illustrates the distal end of a lead 200 having four segmented electrodes 210. In this embodiment, segmented electrode 210 is comprised of two segments, first segment 210a and second segment 210b. Each segment 210a,b has a conductive wire 204 attached thereto and the conductive wires 204 extend along the length of the lead 200 so as to connect with a pulse generator to provide electrical signals to the associated segments. Thus, each segment can be individually energized and techniques such as current steering can be applied to direct stimulation spatially (e.g. direct stimulation current in one or more desired directions). Consequently, segments which are not desirably positioned in relation to the target nerve or other target tissue can receive minimal or no stimulation energy. In some embodiments, different segments can receive different stimulation signals (e.g. according to different programs).

It may be appreciated that the segmented electrodes 210 can have any number of segments, such as two, three, four or more. Likewise, any number of segmented electrodes 210 may be disposed along the lead 200. FIG. 11 illustrates an embodiment of a segmented electrode 210 having a first segment 210a, a second segment 210b, and a third segment 210c. In this embodiment, the segments 210a, 210b, 210c are substantially similar in size. The segments 210a-c can each span approximately 120 degrees around the circumference of the lead 200. If four of these segmented electrodes 210 were disposed along a lead 200, the lead 200 would provide twelve electrode segments. FIG. 12 illustrates an embodiment of a segmented electrode 210 having a first segment 210a, a second segment 210b, a third segment 210c and a fourth segment 210d. In this embodiment, the segments 210a, 210b, 210c, 210d are substantially similar in size. The segments 210a-d can each span approximately 90 degrees around the circumference of the lead 200. If four of these segmented electrodes 210 were disposed along a lead 200, the lead 200 would provide sixteen electrode segments.

As mentioned, such segmented electrodes 210 would typically lie on the outer circumference of the lead shaft 154. In some embodiments, the shaft 154 has an outer diameter ranging from 0.5 mm to 3.0 mm, typically 1.0 mm to 1.35 mm. In some embodiments, the electrode segments 210 have a length (parallel to the lead axis) of 1.0 mm to 5.0 mm, typically 2.5 mm to 4.0 mm. And in some embodiments, the electrodes 202 are spaced apart (parallel to the lead axis) approximately 0.5 mm to 6 mm (edge to edge). The radial gap between electrode segments may range from small (a few degrees; less than 1 mm linear distance in embodiments such as segments 210a and 210b of FIG. 12) to a span approaching 180 degrees (e.g. small contacts on opposite sides of the shaft 154).

Figure 13:
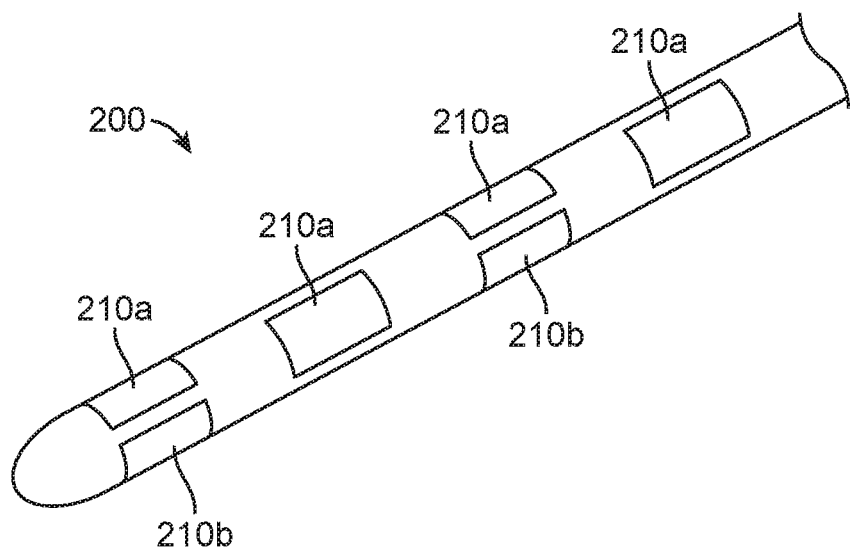
FIG. 13 illustrates an embodiment of a lead having four segmented electrodes of varying orientation.

It may be appreciated that the orientation of the segmented electrodes 210 may vary along the length of the lead 200. For example, FIG. 13 illustrates an embodiment of a lead 200 having four segmented electrodes, each comprised of a first segment 210a and a second segment 210b. The segments 210a, 210b wrap at least partially around the shaft of the lead 200. In this embodiment, the orientation of the segments 210a, 210b shift by 90 degrees around the circumference of the shaft at each position of the four segmented electrodes. In other words, one of the segmented electrodes is positioned so that the first segment 210a is disposed along the "top" of the shaft and another of the segmented electrodes is positioned so that the first segment 210a is disposed along a "side" of the shaft. It may be appreciated that any number and types of spacings or other orientations may be used. Thus, use of the segmented electrodes 210 provides high variability in stimulation energy delivery, allowing for more specific steering of energy. This configuration reduces wastefulness in terms of energy utilization for stimulation, maximizes the probability of having electrodes well positioned relative to the target tissue, and also reduces the possibility of recruitment of other (non-target) neural tissue that can lead to adverse/uncomfortable stimulation.

Segmented electrodes 210 can also be used as an aid in lead placement. By stimulating with the use of a first segment 210a of an electrode and recording Evoked Compound Action Potentials (ECAP) from the corresponding or opposite second segment 210b, a relative measure of the location of the lead 200 can be obtained. Such a measurement is superior to using a single electrode which can have a stimulation artifact. Likewise, using a neighboring electrode in a traditional cylindrical design having ring electrodes is sub-optimal due to the distance between where the stimulation is occurring and where the measurement is made.

When using ECAP with the segmented electrodes of the present invention, measurements can be made and feedback provided to the clinician (e.g. surgeon) as the lead 200 is inserted in the vicinity of the target tissue. These measurements can be made at suprathreshold levels for stimulation of the target tissue. Once the leads are placed, the ECAP can also be used to set stimulation parameters at levels relative to where ECAP is first observed. This method can reduce stimulation levels (and increasing battery life), while avoiding adverse stimulation due to motion, etc.

Current delivered can be fractionalized between electrode segments in order to refine and/or focus the targeting of the nerve. Alternatively or additionally, the ECAP data can be used to determine electrode configuration to further focus stimulation energy toward the target nerve.

In some embodiments, a return electrode is disposed along the proximal end of the lead 200, and used as a remote return electrode during monopolar stimulation. Alternatively or additionally, one or more portions of the INS 150 (e.g. one or more conductive portions of a housing of INS 150) may be used as a return electrode. For example, in some embodiments a metal flange which is part of a feedthrough/enclosure hermetic seal of the INS 150 can be used as a return electrode. In such embodiments, the flange may be comprised of any suitable metal, such as titanium, or other conductive material.

Wireless EMG

Lead placement can also be optimized with the use of electromyography (EMG) also known as compound muscle action potential (cMAP). EMG is performed using an instrument called an electromyograph which detects the electrical potential generated by muscle cells when these cells are electrically or neurologically activated. The signals can be analyzed to assist in desirable lead placement and to assist in setting stimulation levels for the implantable devices.

There are two main kinds of EMG: surface EMG and intramuscular EMG. Surface EMG records muscle activity from the surface above the muscle on the skin or mucous membrane. Surface EMG can be recorded by a pair of electrodes or by a more complex array of multiple electrodes. More than one electrode is needed because EMG recordings display the potential difference (voltage difference) between two separate electrodes. Intramuscular EMG can be performed using a variety of different types of recording electrodes. The simplest approach is a monopolar needle electrode. This electrode can be a fine wire inserted into a muscle, and using a surface electrode as a reference; or two fine wires inserted into muscle tissue, the two wires referenced to each other. To perform intramuscular EMG, typically either a monopolar or concentric needle electrode is inserted through the skin into the muscle tissue.

EMG measurements can be used to ensure desired lead placement and to reduce the duration and complexity of the implantation procedure. Typically, an implantable temporary or permanent lead is implanted in the patient's body near the target area and at least one EMG sensing electrode is positioned nearby on a skin surface or within the patient. A test stimulation is then delivered at a stimulation amplitude level to a nerve tissue of the patient with the use of an electrode on the implantable lead. Test stimulations are selected or adjusted in increments to achieve a desired stimulation-induced EMG motor response. These steps are repeated for each of the electrodes along the implantable lead. A stimulation-induced EMG motor response is recorded or visualized for each test stimulation on each electrode of the implantable lead via the at least one EMG sensing electrode so as to assist in positioning of the implantable lead within a target area. Lead placement can then be further validated and fine-tuned by testing for a stimulation amplitude threshold for each electrode.

As mentioned, the present invention has particular application to sacral nerve stimulation, such as to treat bladder and bowel dysfunctions. In such instances, the implantable lead is positioned in proximity to a sacral nerve root so as to treat the bladder or bowl dysfunction. In some embodiments, the implantable lead comprises at least four stimulation electrodes arranged in a linear array along a length of the lead, wherein at least one of the electrodes is in proximity to the sacral nerve root. In some embodiments, EMG sensing electrodes are positioned on the foot to record EMG signals associated with plantar flexion of the big toe. In such instances, a wireless surface EMG system (custom or off-the-shelf) may be used in conjunction with a clinical programmer to detect the responses. One example of such a system is a Trigno™ Mini Sensor by Delsys Inc. (Natick, Mass.). The EMG sensing electrodes are positioned over and may record activity from the flexor hallucis brevis muscle and/or abductor hallucis muscle. In some embodiments, a second pair of EMG sensing electrodes are positioned within an inner area of the patient buttocks near or over the anal sphincter, such as over the levator ani muscles. These EMG sensing electrodes are positioned to record the anal bellows response of the patient, which represents activation of the levator ani muscles of the perineal musculature. In such instances the anal electrodes can be percutaneous/needle electrodes, surface electrodes, and/or sponge electrodes.

It will be appreciated that the EMG signal processor can also record a stimulation-induced EMG motor response associated with the big toe only or a stimulation-induced EMG motor response associated with the anal bellows only for each test stimulation. The test stimulation delivered by the signal generator comprises at least one electrical pulse below a muscle activation threshold and the EMG sensing electrodes detects stimulation of the nerve tissue.

It may be appreciated that the EMG signal can alternatively be recorded vaginally or at a urethral sphincter. Typically, the urethral electrodes are ring or needle electrodes. The programming of the device can be implemented in a closed-loop fashion where the EMG signal is either maximized or minimized to facilitate the best therapeutic response. EMG is also useful as re-programming device to optimize the stimulation level/electrode configuration. For example, the stimulation can be set at the first observed EMG which will usually occur before any sensory or visible motor response. At such a level the potential of patient discomfort is minimized while still guaranteeing efficacious stimulation.

The manner in which the electrodes are activated, while monitoring EMG, can be systematic or random. For example, when four electrodes are present, electrodes 1 through 4 may be activated in a sequential or random order. Similarly, the stimulation amplitudes delivered to the electrodes may be ascending, descending or random.

User Controls and Feedback Management

Patients who undergo neuromodulation generally "titrate" their therapy over the first few weeks of use. With conventional neuromodulation systems, this titration is accomplished by a remote control that is placed directly over the implant site. Beyond the first few weeks the patient may seldom use the remote control functionality. However, it can be desirable to obtain battery status periodically.

In some embodiments of the present invention, the neuromodulation system comprises an implantable device (that includes a rechargeable implantable battery) and a closely coupled (0.5 cm-3 cm) external RF system used for recharging the implantable battery and/or for bi-directional communications. In such embodiments, a charging system and remote control are utilized and are positioned in close vicinity to the implantable device from time to time so as to charge the implantable battery and communicate with the implantable device. In some embodiments, the remote control system is not a long range link due to reuse of the charging link. In other embodiments, the remote control system is a long range link.

Figure 14:
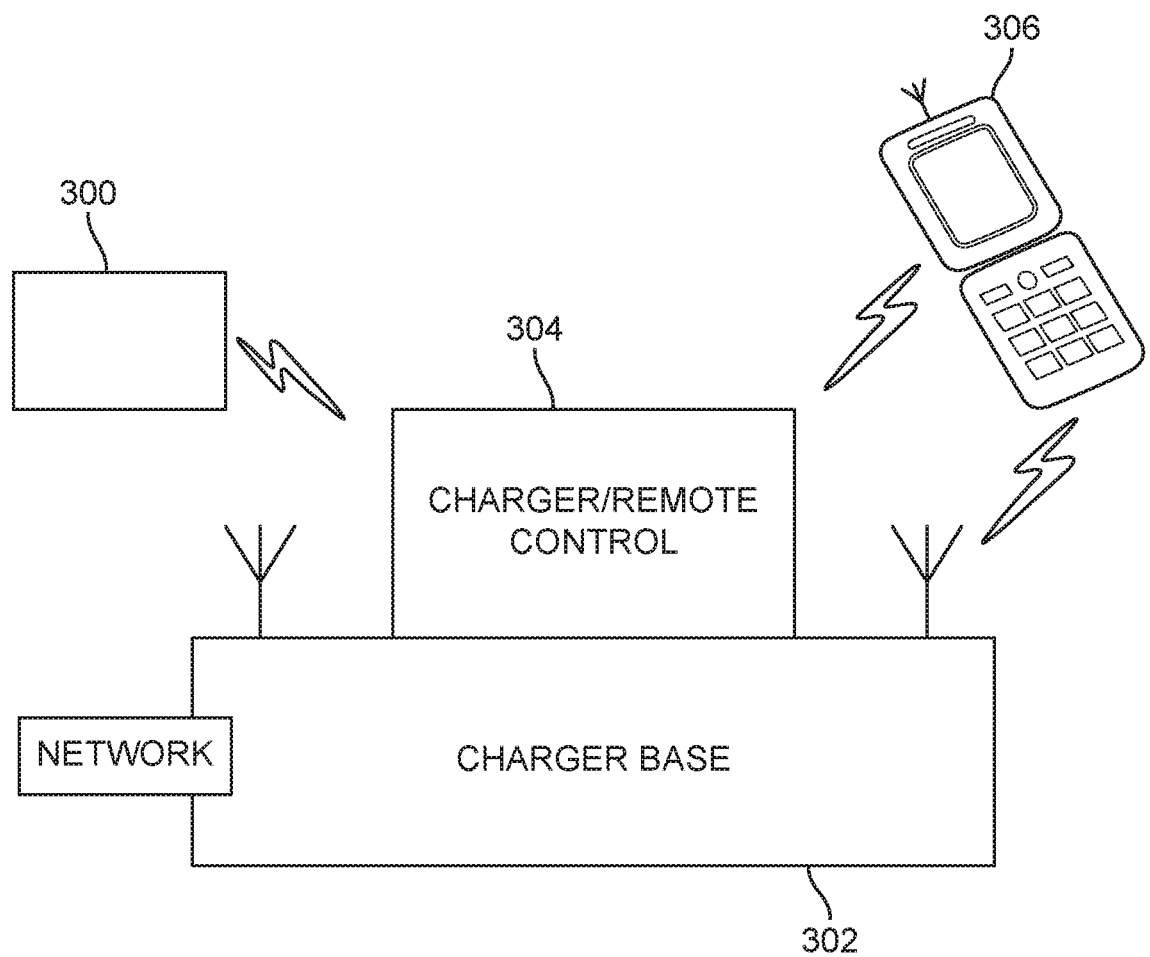
FIG. 14 is a schematic illustration of an embodiment of a neuromodulation system comprising an implantable device, a charger base, a charger/remote control and a hand-held communication device.

FIG. 14 is a schematic illustration of an embodiment of a neuromodulation system comprising an implantable device 300, a charger base 302, a charger/remote control 304 and a hand-held communication device 306. In this embodiment, the communication device 306 is a commercially available smartphone or a device with a smartphone-like industrial design. For example, in some embodiments the communication device 306 has a touchscreen (e.g., a capacitive touchscreen) graphical user interface with virtual buttons and input/output fields. The device 306 may also have tactile buttons that provide quick and simple core system functions. Such smartphone-like design is generally easy for the user to adapt to since smartphones have become very popular and most people are comfortable interacting with a smartphone-like user interface.

In the early weeks of titration, the user can use the communication device 306 to define and modify the therapy and/or the communication device can run an autonomous algorithm to establish therapy modifications. The device 306 sends the parameters to the charger base 302. The next time the charger 304 is placed on the base 302 it receives instructions to be relayed to the implant 300. Later, when the battery within the implant 300 is being subsequently charged, the charger 304 updates the therapy parameters of the implant 300.

In some embodiments, the communication device 306 also collects patient feedback regarding the therapy. For instance, in some embodiments, the communication device 306 functions as a digital diary of: voiding events and/or other unintended sensory events (e.g. pelvic pain), or electrode contact impedances; and/or patient activity levels. This feedback, together with time of day or activity information (e.g. patient activity information), such as from a 3rd party app (e.g. iPhone Health App) or other information, can then be used in real time or retrospectively to either automatically adjust or suggest changes to the stimulation that can be applied to the implantable device 300 via the previously described link.

As previously mentioned, beyond the early weeks most of the interaction of the remote control 304 may be limited to checking battery status. To facilitate this battery monitoring, in some embodiments, the charger 304 collects battery statistics from the implantable device 300 when it charges the battery within the implantable device 300. This information is then conveyed to the communications device 306 via the charger base 302. In other embodiments, the charger base 302 uploads this information to a server, such as a remote cloud server, via a wired or wireless (WiFi/Cell) link. Since the therapy itself is not typically changing much over time, the battery statistics coupled with a battery model can often be used to estimate battery status and be accessible to the user at all times via the communication device 306. This estimation can reduce or even eliminate the need to use the remote control 304 to check battery status when desired by the user. It may be appreciated that, in some embodiments, the charger 304 communicates with the communication device 306 and/or cloud server directly without use of the charger base 302.

To facilitate medically prescribed titration of patient parameters, cloud based request/authorization means may be employed to, for example, notify a healthcare professional when particular events occur. Such events may include information gleaned from voiding diaries, unintended stimulation events or repetitive user actuated UI events to increase or decrease stimulation outside prescribed bounds at time of initial fitting. In response, upon health professional review, electronic updates to make more prescriptive changes to the stimulation program could be delivered via a cloud server to the implantable device 300. This reduces needs for office visits while safely improving patient care.

Post implantation, digitized medical imaging (e.g. x-ray) data can be attached to a patient record and stored within a user/doctor accessible software application. Such data may then be readily available in the future for use. For example, if there is a shift in stimulation sensitivity, such as due to a migrated lead, the stored medical imaging data can be compared against new imagery to assist in reassigning stimulation weights to different electrodes (linearly, segmented, etc.) on the implantable lead to restore original efficacy of therapy. Likewise, such data can be used with chronological impedance data to make such suggestions for reassigning stimulation weights.

The communication device 306 can also provide lifestyle application features to help patients adapt to the use of their implantable device 300. In some embodiments, "charge event reminders" can be integrated with the patient's electronic calendar. Likewise, a periodic calendar appointment can be added to their electronic calendar or short message service (SMS) messages can be delivered to remind patients of the need to charge or take other actions (e.g. SMS messages: "estimated remaining time to recharge: 18 hours", "Health App detects that you have been walking for >2 miles: initiation of extra therapy cycle recommended").

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A stimulation system comprising:
    an implantable device comprising:
        a flexible shaft having a proximal end and a distal end, and at least one electrode along the distal end, the flexible shaft comprising a plurality of tines extending therefrom at a position along the flexible shaft proximal of the at least one electrode, wherein the at least one electrode comprises at least one set of segmented electrodes, and wherein the flexible shaft is configured to be implanted adjacent to a nerve in a peripheral nervous system;
        an implantable neuromodulation stimulator (INS) having a housing that is disposed along and integral with the proximal end of the flexible shaft, wherein the housing of the INS and the proximal end of the flexible shaft are a unitary structure; and
        an external device comprising a battery, a transmitter, and an antenna, wherein the stimulation system is configured to determine a relative measure of a location of the implantable device using the at least one set of segmented electrodes and electromyography (EMG) to assist in placement of the implantable device.

2. The stimulation system according to claim 1, wherein the external device transmits one or more of power and data to the implantable neuromodulation stimulator.

3. The stimulation system according to claim 2, wherein the external device transmits power and data to the implantable neuromodulation stimulator.

4. The stimulation system according to claim 1, wherein the external device comprises one or more of an interface and an autonomous control algorithm to control therapy and/or monitor therapy effectiveness.

5. The stimulation system according to claim 1, wherein the implantable device is configured to be implanted in the patient for a time period selected from the group consisting of: less than 2 days; less than 1 week; less than 1 month; at least 1 month; at least 3 months; at least 6 months; and combinations thereof.

6. The stimulation system according to claim 1, wherein the implantable neuromodulation stimulator comprises non-adjustable functional parameters.

7. The stimulation system according to claim 1, wherein the external device comprises a housing that is hermetically or non-hermetically sealed.

8. The stimulation system according to claim 1, wherein the external device comprises a housing configured to provide a water-resistant barrier.

9. The stimulation system according to claim 1, wherein the external device comprises at least one encapsulant configured to reduce moisture ingress.

10. The stimulation system according to claim 1, wherein the flexible shaft is cylindrical and has a paddle shaped distal end.

11. The stimulation system according to claim 1, wherein the at least one electrode comprises two or more electrodes including longitudinal and lateral spans to cover concurrent stimulation sites.

12. The stimulation system according to claim 11, wherein the at least one electrode comprises twelve independently programmable electrodes across three columns.

13. The stimulation system according to claim 1, wherein the flexible shaft has a length that correlates to the anatomical positioning of the implantable device.

14. The stimulation system according to claim 1, wherein the implantable neuromodulation stimulator is configured to provide one or more of bilateral stimulation and unilateral stimulation at multiple target locations.

15. The stimulation system according to claim 14, wherein the multiple target locations comprise multiple locations within multiple foramina.

16. The stimulation system according to claim 1, wherein the external device is configured to gather information regarding one or more of: the implantable neuromodulation stimulator; the patient; and the patient's environment.

17. The stimulation system according to claim 1, wherein the implantable neuromodulation stimulator comprises an implantable battery and an implantable antenna that comprises a printed circuit board (PCB) antenna.

18. The stimulation system according to claim 17, wherein the implantable antenna surrounds the implantable battery.

19. The stimulation system according to claim 1, wherein the at least one electrode comprises a plurality of sets of segmented electrodes and the plurality of sets of segmented electrodes comprises a first set and a second set, and wherein the first and second sets of segmented electrodes are positioned at different longitudinal positions along the flexible shaft.

20. The stimulation system according to claim 1, wherein the at least one set of segmented electrodes is configured to focus and steer current delivery.

21. The stimulation system according to claim 1, further comprising a communication device configured to perform a function selected from the group consisting of: define the therapy to be delivered by the system; modify the therapy to be delivered by the system; run an algorithm to establish therapy modifications; and combinations thereof.

22. The stimulation system according to claim 21, wherein the communication device comprises a smart phone.

23. The stimulation system according to claim 21, further comprising a charger and charger base, wherein the communication device transmits information to the charger base, wherein the charger receives the information from the charger base, and wherein the charger sends the information to the implantable neuromodulator stimulator.

24. The stimulation system according to claim 23, wherein the implantable neuromodulation stimulator comprises an implantable battery wherein the charger is configured to collect battery statistics from the implantable neuromodulation stimulator during charging of the implantable battery.

25. The stimulation system according to claim 24, wherein the charger is configured to upload the battery statistics to a server via one or more of a wired link and a wireless link.

26. The stimulation system according to claim 25, wherein the server comprises a remote cloud server.

27. The stimulation system according to claim 21, wherein the communication device is configured to gather patient feedback, and wherein the system adjusts the stimulation based on the gathered patient feedback.

28. The stimulation system according to claim 27, wherein the stimulation adjustment is further based on one or more of time of day information and activity information.

29. The stimulation system according to claim 1, wherein the implantable neuromodulation stimulator is configured to provide stimulation to treat one or more of a pelvic disorder, acute pain, or chronic pain.

30. The stimulation system according to claim 1, wherein the implantable device further comprises one or more anchors or tines configured to extend from the flexible shaft.

* * * * *